United States Patent [19]

Bridoux et al.

[11] 4,204,435

[45] May 27, 1980

[54] DEVICES USING ULTRASOUNDS FOR FORMING IMAGES, IN PARTICULAR FOR THE INTERNAL EXAMINATION OF THE HUMAN BODY

[75] Inventors: Edouard Bridoux, Maing; Christian Bruneel, Marly; Francis Haine; Guy Thomin, both of Valenciennes, all of France

[73] Assignee: Agence Nationale de Valorisation de la Recherche (ANVAR), Neuilly sur Sein, France

[21] Appl. No.: 900,665

[22] Filed: Apr. 27, 1978

[30] Foreign Application Priority Data

Apr. 29, 1977 [FR] France .................. 77 12994
Apr. 17, 1978 [FR] France .................. 78 11274

[51] Int. Cl.² ............................................. G01N 29/00
[52] U.S. Cl. ................................ 73/626; 128/660
[58] Field of Search ............. 73/625, 626, 628, 641, 73/642; 128/2 V, 2.05 Z, 660

[56] References Cited

U.S. PATENT DOCUMENTS 3,269,173  8/1966  Von Ardenne ................ 73/642
3,402,598  9/1968  Colgate ........................... 73/642
3,922,907  12/1975 Hurwitz et al. .................. 73/642

FOREIGN PATENT DOCUMENTS 2303289 10/1976 France .................. 73/626

Primary Examiner—Stephen A. Kreitman
Attorney, Agent, or Firm—Freilich, Hornbacker, Wasserman, Rosen & Fernandez

[57] ABSTRACT

The invention relates to a probe for a device forming images from ultrasounds, in particular for the internal examination of the human body. The probe comprises transducers distributed in a curved array providing the possibility of a sectorial angular scanning and of generating ultrasonic beams converging towards a localized area where is arranged either a screen opaque to ultrasounds and formed with one or two openings in the vicinity of the center of converging area, with one or two lenses for ultrasounds in said opening or openings, either one or two electronic lenses formed with means for converting in parallel ultrasounds into electric signals, apparatus for differentially delaying the electric signals and apparatus for converting in parallel the electric signals, after a delay, into ultrasounds.

4 Claims, 22 Drawing Figures

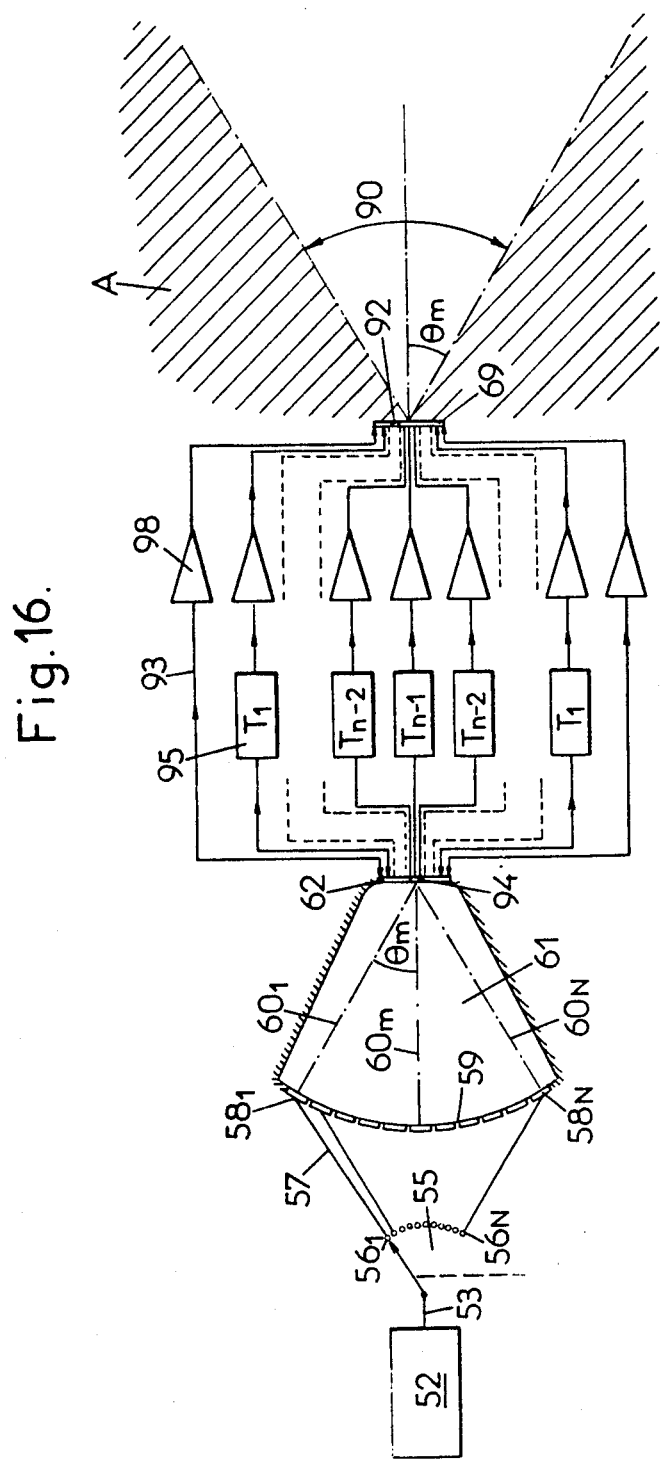

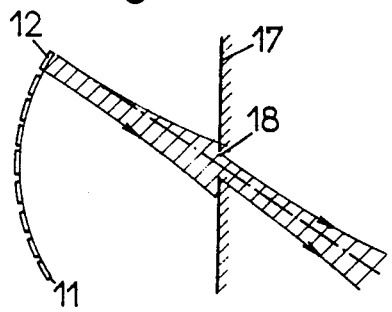
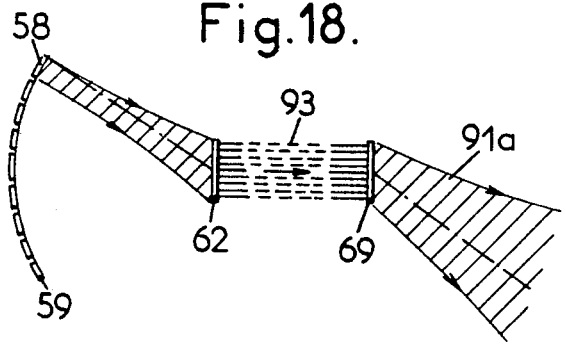
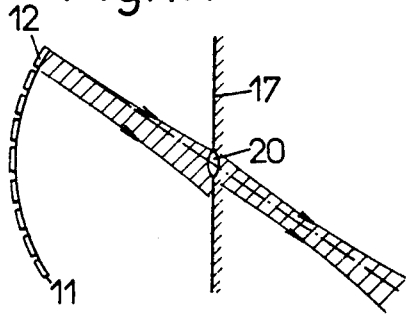
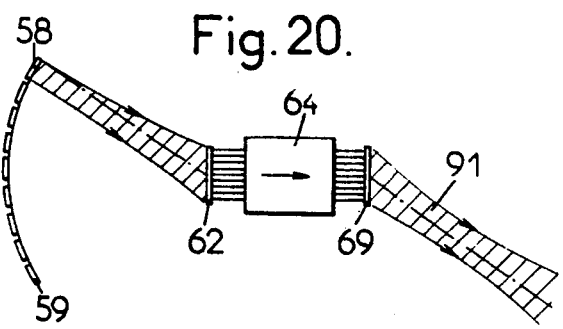
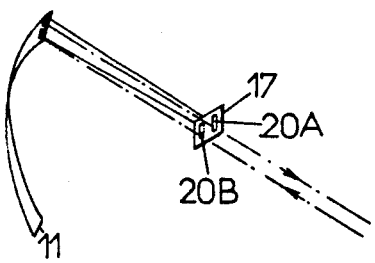
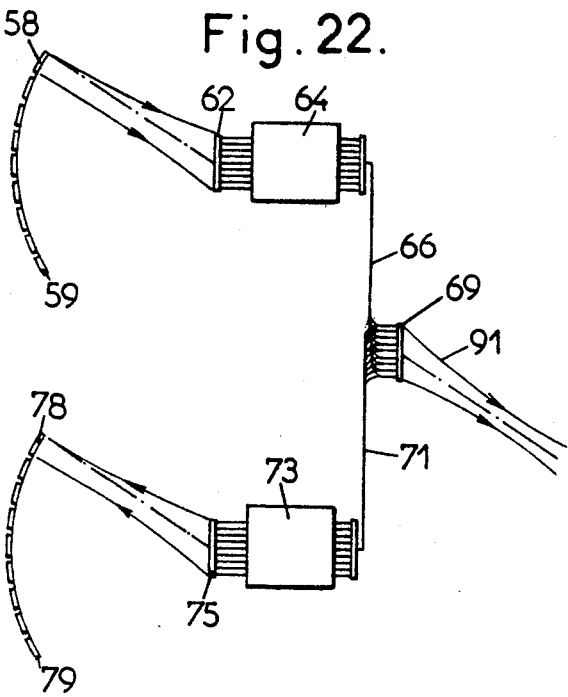

DEVICES USING ULTRASOUNDS FOR FORMING IMAGES, IN PARTICULAR FOR THE INTERNAL EXAMINATION OF THE HUMAN BODY

BACKGROUND OF THE INVENTION

The present invention relates to the formation of images by means of ultrasounds.

It relates more particularly to the formation of internal images of objects, optically opaque, through ultrasonic echography.

A device according to the invention provides the formation, instantaneously and continuously, of visible representations of the section of a heterogeous body having discontinuities, even mobile.

Such a device is particularly adapted to medical applications, as it provides the possibility of observing internal anatomic structures of a living being without discernible disturbances.

Of course, the ultrasonic echography device according to the invention has other applications than in the medical observation field, but it is for this application where the requirements are the most exacting that the device is particularly appropriate.

There is already known ultrasonic echography devices for the formation of images of internal objects, optically opaque.

Said devices differ between themselves substantially by their shape and the operating principle of the ultrasonic captor.

The apparatus with parallel beam plane probe comprise an ultrasonic transmitter-receiver formed of one or two series of elementary transducers positioned side by side, each elementary transducer converting the received electric energy into transmitted ultrasonic vibrations and/or converting the receive ultrasonic energy into a variable electric voltage, and a switching unit supplying in succession and cyclically the various transducers with electric pulses from a pulse generator in order to provide transmission of the ultrasonic pulses from the transducers, and which switches off the electric signals resulting from the conversion of ultrasonic echos sent back by the observed object and picked up by the transducers, in succession and cyclically, towards signal processing means supplying a visualizing device.

The sectorial analysis of a section may be obtained by means of a small dimension transmitter-receiver vibrating mechanically, or by means of a stationary transmitter-receiver generating an analysis beam reflected by a vibrating mirror, either through an array of transducers energized according to programmed sequences so that the ultrasonic beam, focused, has a variable direction and that the analysis area be sectorial.

The prior devices using non focused beam probes, use diverging ultrasound beams since there is no diffraction compensation. The section of each analysis beam increases as the distance from the transmitting transducer increases. Two reflecting objects therefore, of a section inferior to that of the analysis beam, are not differentiated. The smallest section which the system can form determines the system definition.

The object of the invention is to provide, by means of a very simple construction, similar performances to that of the prior devices, while extending the medical applications of said devices through a diminution of the area of the surface of the human body through which pass the ultrasounds.

The prior apparatus, with a flat probe, comprise actually either a simple unit supplying images of very insufficient definition (from about 6 mm to 10 mm), or a very complex unit piloted in certain cases by a powerful computer forming images having a definition near the theoretical value of half the wave length of the ultrasounds used.

In both cases, the total surface of the probe in contact with the biological milieu is important (10 cm$^2$ about).

The contact area of the probes acting through a sectorial mechanical scanning is more reduced than previously; however, this advantage is largely offset by the disadvantages inherent the mechanical systems (wear, vibrations, slow cadence).

SUMMARY OF THE INVENTION

The object of the invention is an electronic scanning probe designed such that all the analysis beams travel through one same area in space, of section close to that of an elementary beam, situated at the probe-body interface to analyse.

According to the invention, the probe cumulates the advantages of non focused probe systems with electronic switching (fast image cadence), those of mechanical scanning systems (contact surface reduced to 1 cm$^2$ about) and some of the electronic scanning and focusing systems (focusing and great depth of field).

A device for forming images by ultrasound echography according to the invention comprises, in known manner, one or two series of individual transducers transmitting, in response to triggering electric signals, ultrasonic signals towards an object to examine and/or transforming the received ultrasonic signals into electric signals, means for applying triggering electric signals to the single series of transducers or to the series providing transmission of ultrasonic signals and means for forming an image from the electric signals provided by the single series of transducers or the series of transducers for the reception of the ultrasonic signals, and is characterized in that the single series or each series of transducers is arranged along a curved band, in such manner as to direct the ultrasound waves, when transmitting as well as receiving, through a reduced area surrounding the center of curvature of the band or of each curved band.

In a first series of embodiments, the device comprises a screen opaque to ultrasounds travelling through the center of curvature of the band or of each curved band and formed with an opening about the center of curvature of each of the centers of curvature.

Preferably, there is foreseen in order to improve the quality of the image, either a lens occupying the screen opening when the device comprises a single series of transducers effecting the conversion of the electric energy into ultrasound energy and vice versa, and a single opening in the screen, or a lens in each opening when the device comprises two series of transducers, one for the transmission of ultrasound waves and the other for the reception of ultrasound waves and the screen being formed with two openings. The lenses used are ultrasound lenses; in the first case, the lens is suitable for the focusing of the transmitted ultrasounds on the one hand and the reflected ultrasounds on the other hand, whereas in the second case the lens which occupies the center of curvature of a series of ultrasounds transmitting transducers is designed for focusing the transmitted ultrasound beam, whereas the lens which is placed in the center of curvature of the series of transducers receiving the ultrasound beam provides focusing of said beam.

The essential interest of using two lenses is to increase the probe depth of field, that is the scanning area in which at least one of the ultrasound beams remains with a section which is inferior to a value determined by the desired definition.

In a second series of embodiments, the device comprises, instead of ultrasound lenses, electronic means for forming electronic lenses, after conversion of the ultrasounds into electric signals and before reconversion of the delayed electric signals into ultrasounds.

It is known that the function of an optical or ultrasonic length is to increase the path of travel for the optical or ultrasound waves the less remote from the axis in order that for one source point (optical or ultrasonic) corresponds an image point, the travel durations of the optical or ultrasound waves from the source point and leading to the image point being the same (focusing effect).

The electronic means used in the present invention provide different predetermined electric delays on the various paths of travel for ensuring the same function as the ultrasonic lenses used in the main patent. In order to implement said delay electronic means, there is foreseen, on the one hand on the transmitting side, the conversion of the ultrasound signals transmitted by the transmitting transducers as electric signals and the reconversion of said electric signals, after processing by delay electronic means, into ultrasonic signals retransmitted towards the object to examine, and on the other hand on the receiving side, the conversion of the ultrasonic signals sent back by said object as electric signals and the reconversion of said electric signals, after processing by the delay electronic means, in ultrasonic signals retransmitted towards the receiving transducers.

Generally, the two transmitting and receiving routes are separate, thereby necessitating, in cooperation with a series of individual transmitting transducers and a series of individual receiving transducers, two distinct delay electronic means, two converters of ultrasonic signals into electric signals and two converters of electric signals into ultrasonic signals for forming two electronic lenses, one for the transmission and the other for the reception with however the special feature that the transmitting converter of electric signals into ultrasonic signals and the receiving converter of ultrasonic signals into electric signals may be merged into one single unit forming a small dimension probe for being easily positioned against the object to be observed, for instance against the rib cage, between two ribs, for observing the heart of a living being.

Consequently, a device for forming images through ultrasonic echography according to this second series of embodiments comprises one or two series of individual transducers transmitting in response to triggering electric signals, ultrasonic signals towards an object to be examined and/or transforming received ultrasonic signals into electric signals, means for applying triggering electric signals to the signal series of transducers or to the series providing transmission of ultrasonic signals and means for effecting the formation of an image from the electric signals supplied by the single series of transducers or the series of transducers providing reception of the ultrasonic signals, a single series or each series of transducers being arranged according to a curved band, and is characterized in that it comprises at least one electronic lens formed of a first array of ultrasonic transducers arranged in the vicinity of the center of curvature of the band or of each curved band, through differential delay electronic means and through a second array of ultrasonic transducers.

Advantageously, the device comprises two curved bands of transducers and two electronic lenses comprising, each, a first array of transducers arranged in the vicinity of the center of curvature of each curved band, differential delay electronic means and a second array of transducers, the second array of the first electronic lens and the second array of the second electronic lens, possibly amalgamated, constituting a probe adapted to be placed against the object to be examined.

It is possible to foresee means whereby one can modify, according to wish, the delay applied by the various elements of the delay electronic means.

BRIEF DESCRIPTION OF THE DRAWINGS

In any case the invention will become more apparent from the following further description, when taken in conjunction with the accompanying drawings, said further description and drawings being of course given mainly by way of exemplification, drawings wherein: p

Figure 5:
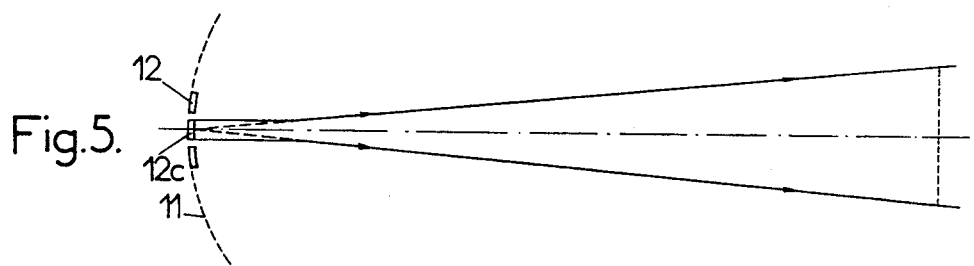
FIGS. 5 through 8 illustrate schematically the path of travel of the ultrasonic beam in the case of transducers arranged according to curved bands, respectively in the four following cases.
Figure 6:
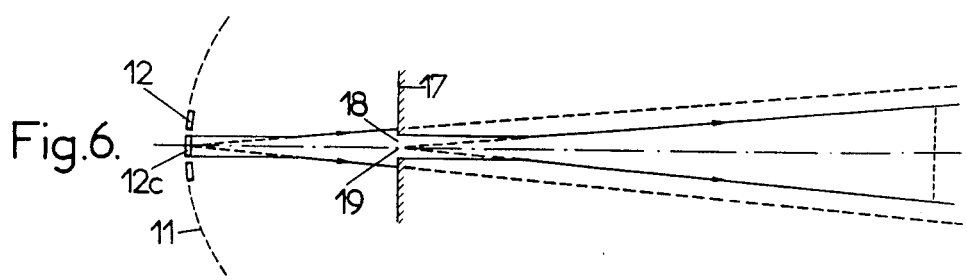
Figure 7:
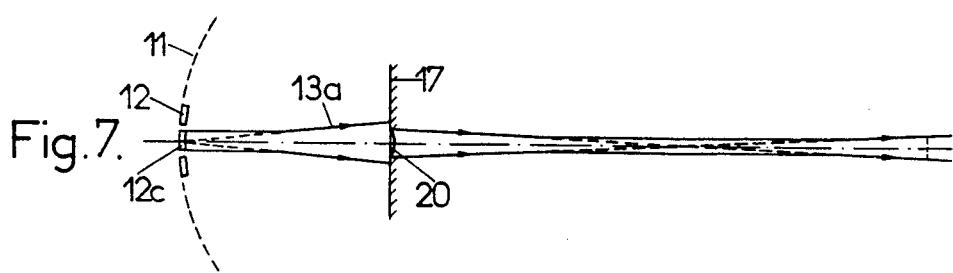
Figure 8:
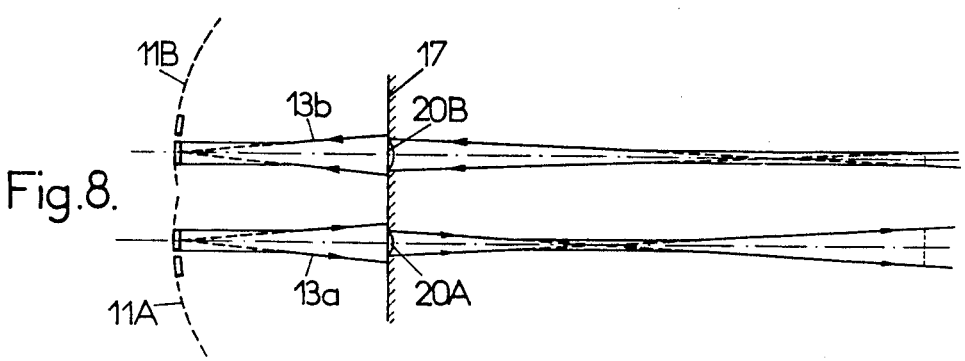

without screen (FIG. 5);

with a screen formed with an opening (FIG. 6);

with a screen formed with an opening in which is diposed a lens (FIG. 7);

with a screen formed with two openings in which are arranged two lenses through which pass, in one of them the transmitted ultrasonic beam and the in the other one the reflected ultrasonic beam, in the case of a device comprising two series of transducers (FIG. 8).

Figure 9:
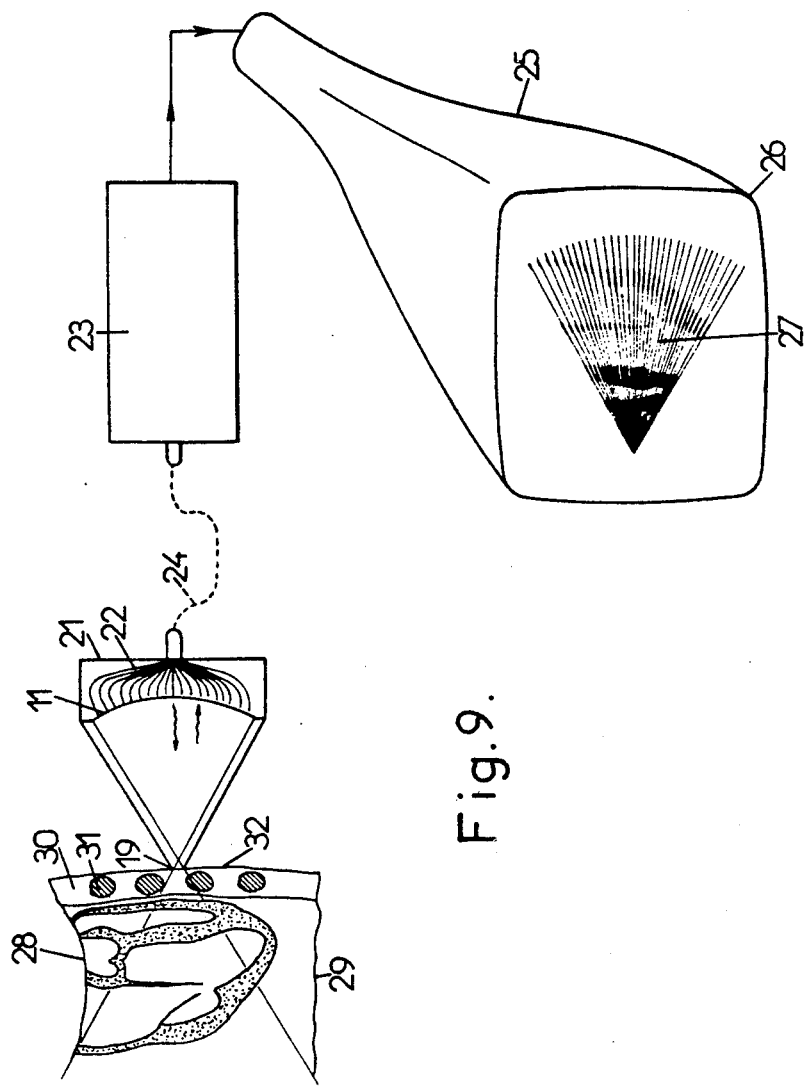
Figure 10:
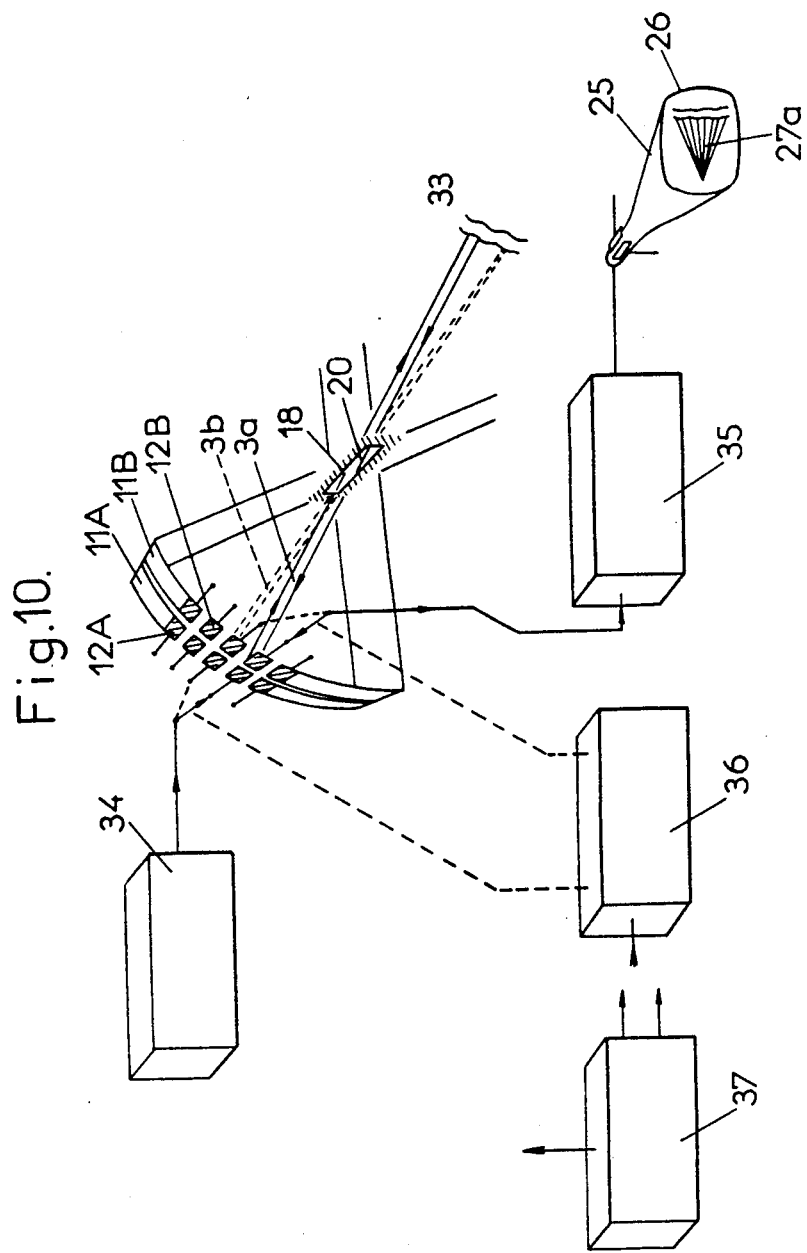

FIGS. 9 and 10 represent schematically two devices according to the first series of embodiments according to the invention, FIG. 9 corresponding to the case of a single array for the ultrasonic transmission and reception, and FIG. 10 to the case where there is foreseen two distinct arrays for the ultrasonic transmission and reception.

Figure 11:
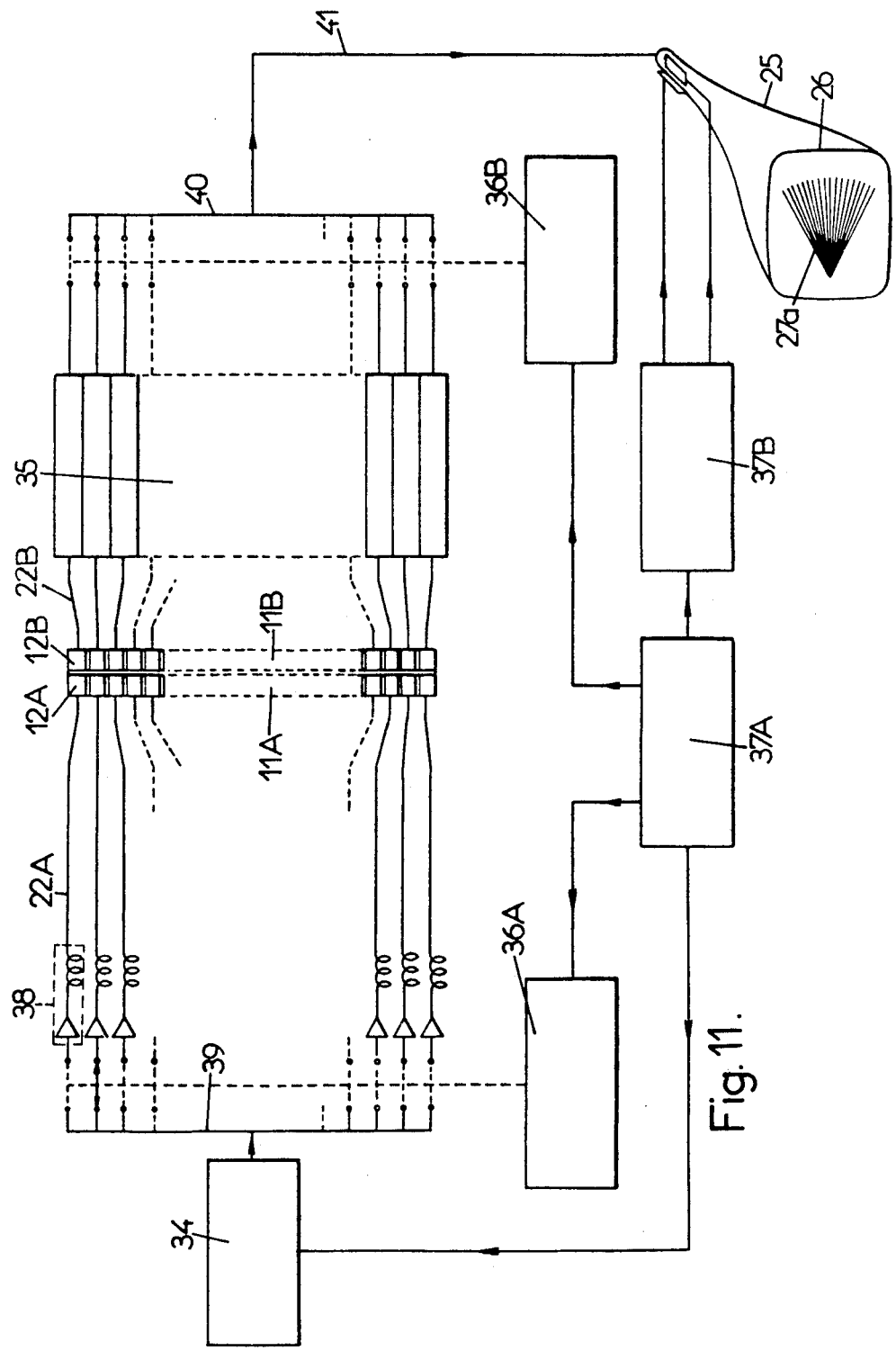

FIG. 11 illustrates, in a more detailed manner, the embodiment schematically shown in FIG. 10.

Figure 12:
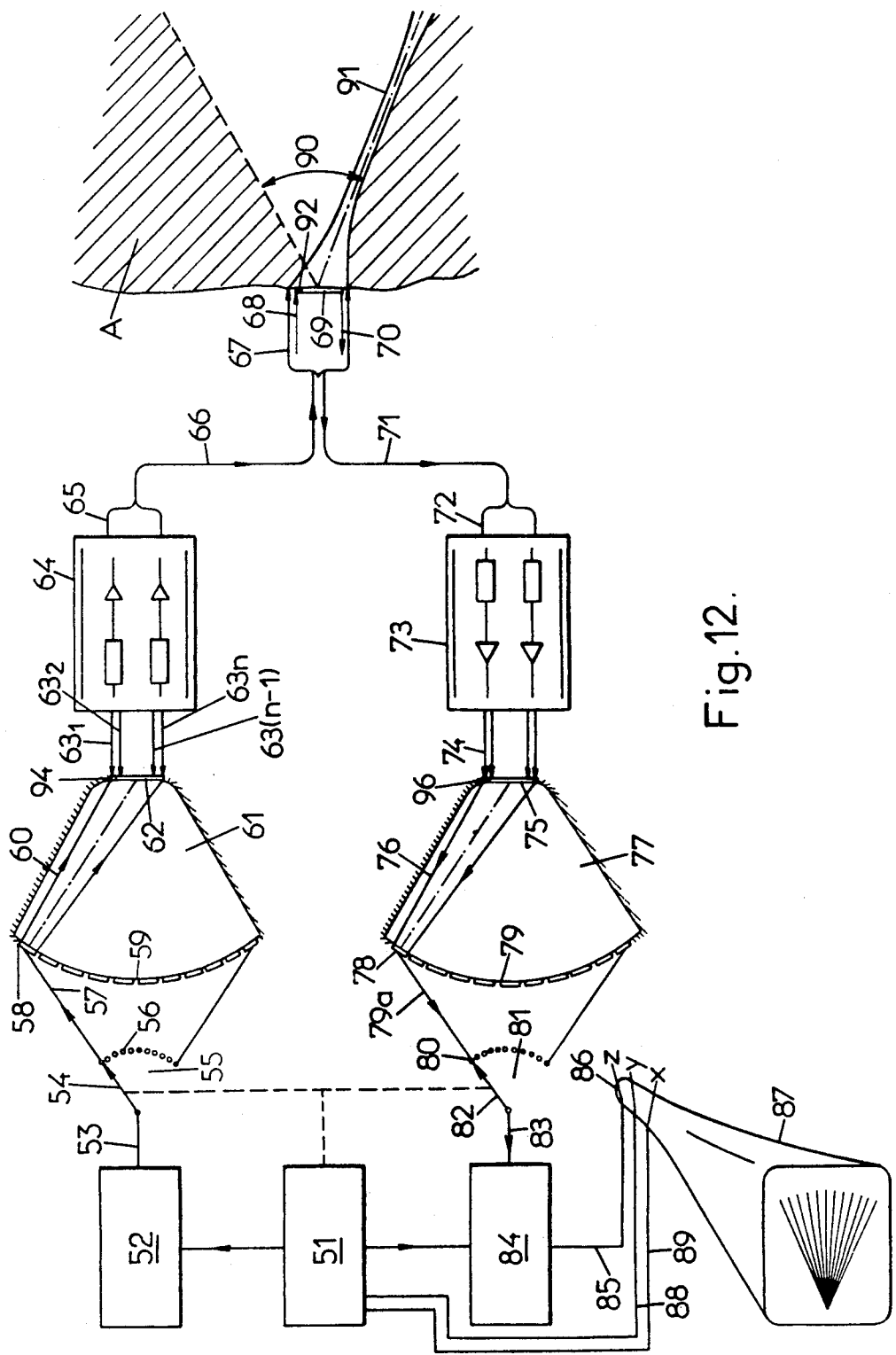

FIG. 12 is a schematic illustration of an ultrasonic examination device provided with the improvements according to the invention, comprising electronic lenses as per the second series of embodiments of the invention.

Figure 13:
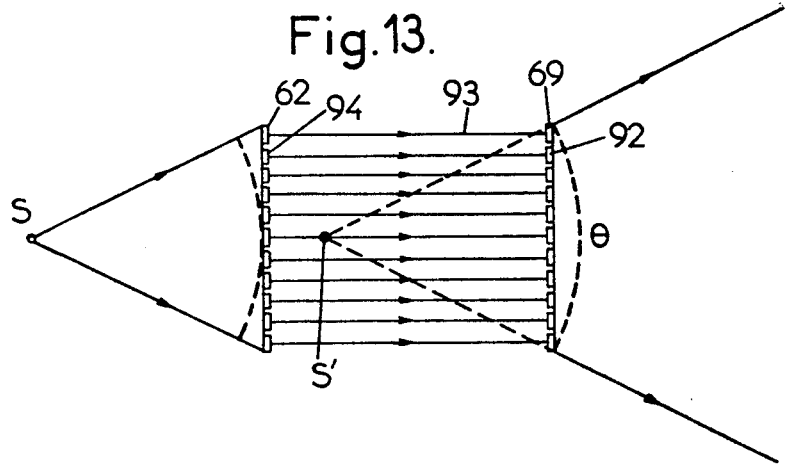
Figure 14:
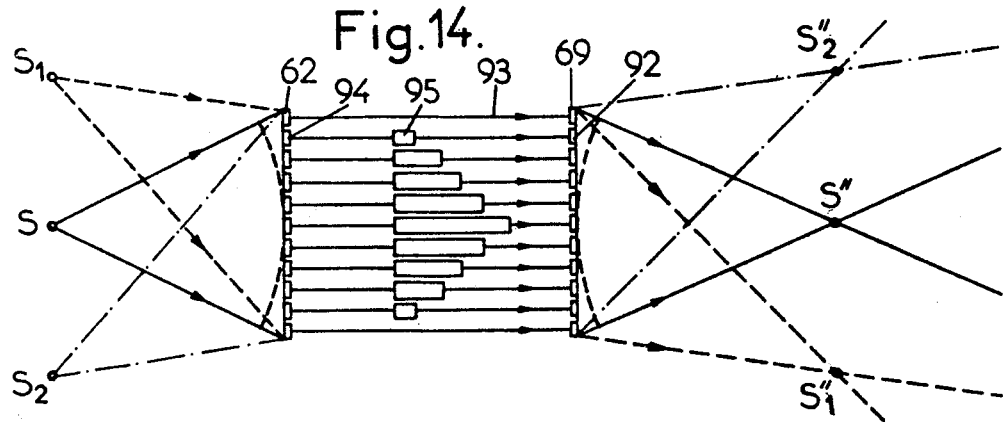
Figure 15:
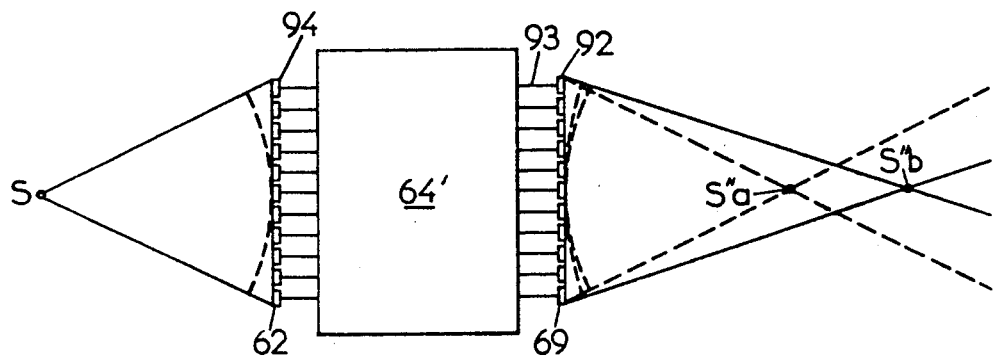

FIGS. 13 through 15 provide explanation for the operation of the electronic lenses of the device of FIG. 12.

FIG. 16 shows in more detail the transmission route of the device according to FIG. 12.

FIGS. 17 through 22 illustrate the function of the lenses of the device of FIG. 16.

According to the invention proposing to provide a device for forming images through ultrasonic echography and particularly suitable for the internal examination of the human body, the procedure is as follows or similar to what will now be explained.

DESCRIPTION OF THE PREFERRED EMBODIMENTS

Figure 1:
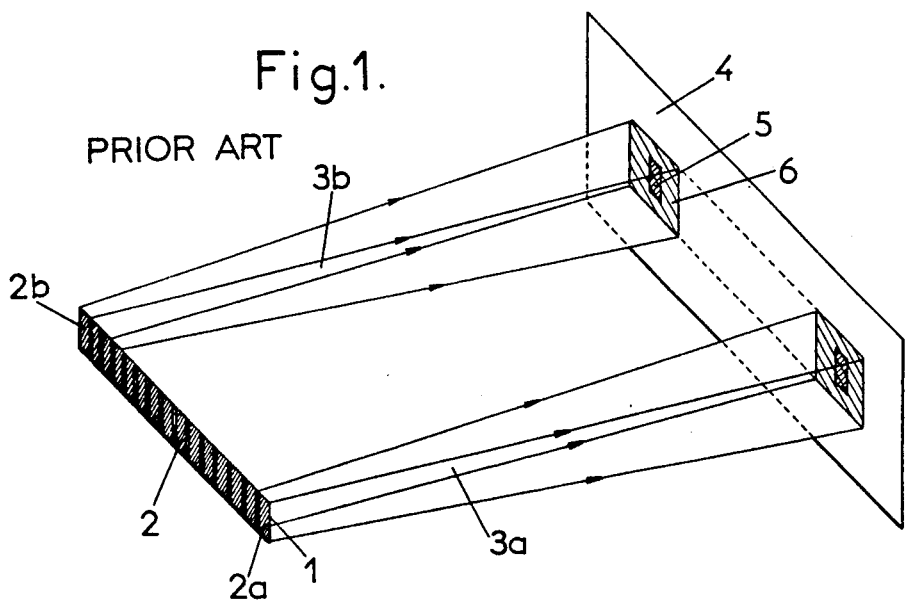
FIG. 1 is a schematic representation of a portion of device with a single series of transducers arranged according to a plane band as per the prior art.

Before this description of a device according to the invention, it should be first recalled, with reference to FIG. 1, that there exists devices for forming images through ultrasonic echography, which comprise a series 1 of N elementary transducers 2 arranged side by side according to a band and which:

on the one hand provide transmission of an ultrasonic beam in response to an electric excitation, and on the other hand transform an ultrasonic beam, as a matter of fact a beam reflected by the object to be observed and making an echo, into an electric signal which is a function of the intensity of the collected ultrasonic signal.

In FIG. 1 has been shown, on the one hand, the extreme positions of the analysis beam transmitted in succession by each of the N elementary transducers 2 forming series 1, viz. positions 3a (of the beam transmitted by transducers 2a) and 3b (of the beam transmitted by transducer 2b) and, on the other hand, the analysis plane 4 at a given moment, which moves away from the transducers at the ultrasound propagation speed.

Each transducer 2 is only connected to the visualization receiving-transmitting unit during the time needed for the formation of one line of the image (corresponding to the time of travel from the probe to the most remote structure and back to the probe) of the ultrasounds (200 microseconds for a depth of 15 cm). An adjacent transducer is energized only when the ultrasonic wave reflected by the most remote structure has set in vibrations the transducer used as an electric mechanical converter.

At each point of the analysis plane corresponds a point of the visualization screen and one only, the brilliancy of which is a function of the intensity of the received wave. On plane 4 has been represented at 5 the area which is most "illuminated" by the ultrasonic beam 3b, and at 6 the "penumbra" area receiving less ultrasounds.

The transducers are formed with ceramics of the metallized PZT type on both faces. The elementary surfaces are obtained by grinding or chemical attack of one or both faces.

The device according to FIG. 1 has the disadvantage that the transducers 2 transmit and receive ultrasonic beams which are not stopped down nor focused, hence a bad definition of the images and, when an organ or a tissue inside a living system has to be observed, this device requires an important contact surface with the skin of the patient (of the order of 10 cm$^2$).

Figure 2:
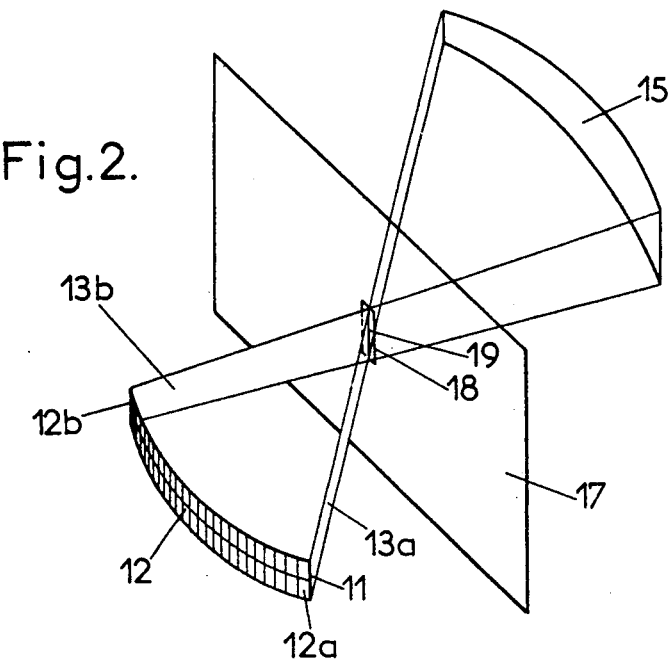
FIG. 2 is a schematic representation of a portion of a device according to the invention with a single series of transducers arranged according to a curved band and with a screen formed with an opening about the center of curvature of said curved band (where the extreme positions only of the transmitted beams have been materialized, at different times, respectively from transducers 12a and 12b).

According to the essential characteristic of the invention illustrated in FIG. 2, the plane array 1 of transducers 2 according to the prior technique (illustrated in FIG. 1) is replaced by a curved array 11, for instance in the form of an arc of a circle, comprising a series of N transducers 12 of the same type as transducers 2 (a ceramic of the metallized PZT type on both faces); within the scope of the first series of the embodiments of the invention, one foresees a screen 17 formed with a slot-shaped opening 18 arranged around a center of curvature 19 of the array 11 in such manner as to stop down the ultrasonic beams, viz. as well a beam transmitted by a transducer (as beam 13a transmitted by transducer 12a) as a beam reflected by an obstacle situated in the scanning area which is beyond the slot.

The obstacle struck by the ultrasounds retransmits an acoustic wave in all directions, in particular according to the direction transducer-slot-object 12a. This return wave is again stopped down when passing through the slot. It strikes then the transducer 12a and the adjacent transducer or transducers. However, the electric signal supplied by transducer 12a is the only one to be used since it is the only one which is connected to the receiver.

In FIG. 2 has also been shown the other extreme ultrasonic beam 13b transmitted by transducer 12b.

In FIG. 2, one sees the area 15 which is observed at a given moment t and one establishes that the contact between the devices and the patient skin, in case of the internal observation of a human body, may be limited to a very small area corresponding to slot 18. This is most advantageous where it is the human heart which is to be observed, in which case the slot 18 is disposed between two ribs, viz. in a position where the passage of ultrasounds is easy. This is not possible with a device of known type according to FIG. 1 which requires a large contact surface comprising generally several ribs which form an obstacle for the passage of the ultrasounds.

In particular, slot 18, the dimension of which are a function or the ultrasounds frequency, of the radius of curvature of the array and of the desired definition, has a section of about 1 cm$^2$ it plays then the role of the diaphragm.

The curved array 11 in FIG. 2 comprises two series of N transducers, one for the transmission and the other for the reception, but is obvious that one can foresee a single series of N transducers which are used for the transmission as well as for the reception (as is the case for the plane array of FIG. 1).

Figure 3:
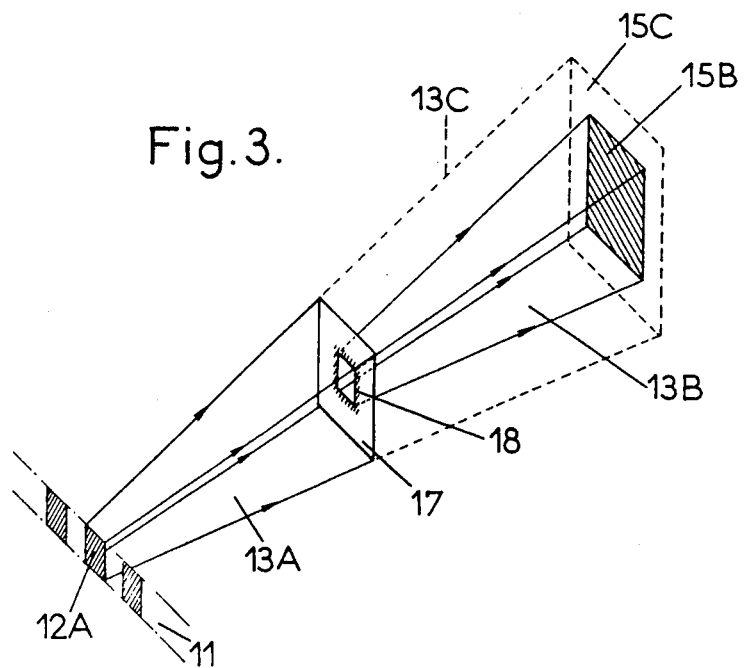
FIG. 3 illustrates the effect of the slot on the geometry of the transmitting ultrasonic beam in the analysed section.

In FIG. 3 has been shown the beam 13A transmitted by the active transmission transducer 12A and its limitation to beam 13B after having passed through opening 18 (the prolongation of beam 13A, had there been no screen, having been shown in dotted lines at 13C). In the analysis plane has been shown at 15B and 15C the areas struck by beams 13B and 13C respectively, that is with the screen with the opening and without screen respectively. One sees easily the effect of the diaphragm produced by screen 17 and slot 18.

Figure 4:
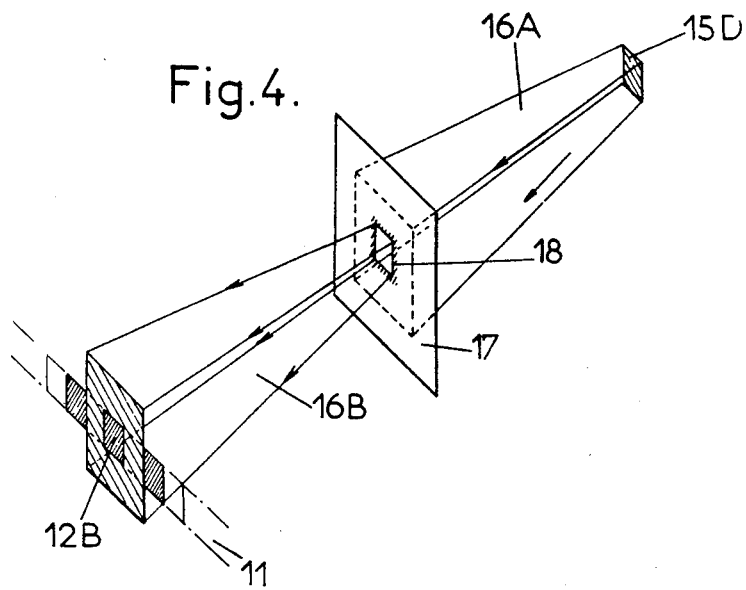
FIG. 4 shows the effect of the slot on the geometry of the beam reflected by a plane obstacle, in the area comprised between the slot and the receiving transducer.

In FIG. 4 has been shown the effect of the diaphragm on beam 16A reflected by area 15D. Screen 17 limits this beam 16A to beam 16B which has passed through opening 18; the stopped down beam 16B strikes one active receiving transducer 12B only.

In FIG. 5 has been shown schematically the beam transmitted by a transducer such as 12c and there is no screen 17 and no slot 18, that is without diaphragm. There is then diffraction.

The implement of a screen 17 with a slot 18 provides, as is shown in FIG. 6, reduction of said diffraction since the slot plays the role of a secondary source for the transmission as well as for the reception of the ultrasonic beam by the transducers. The slot 18 thins down therefore twice each elementary beam, mainly when the ultrasounds pass through it when being transmitted and for the reception (as explained with reference to FIGS. 3 and 4).

In FIG. 7 is shown the advantage provided when there is arranged in slot 18 a lens 20 for the ultrasounds, said lens limitting still further the diffraction.

When a lens 20 is foreseen, each scanning unitary beam, such as beam 13a, has a smaller thickness, and the same applies to the reflected beam, which improves the lateral definition. Moreover, the lens 20 allows to increase, with an equal opening, the number of transmitters, and thereby the image fineness.

Finally and as is shown in FIG. 8, one may foresee not only one single array 11 for the transmission and reception of the ultrasonic beams, but two arrays 11A and 11B, the first one being provided for the transmission and the second one for the reception. In this case, there are foreseen two lenses 20A and 20B for the ultrasounds, one of them acting on beam 13a which is being transmitted and the other on the reflected beam 13b.

The embodiment of the probe with two arrays is justified by the fact that the transmitting transducer is constantly insulated from the receiving transducer, which facilitates the manufacture of the switch providing the sequential connection of each of the receiving transducers with the low sound preamplifier, since the pulses which are applied to the transmitting transducer are no more applied to the input of said switch.

On the other hand, due to the fact that the two transmitting and receiving transducers are in the same plane, there is less energy which is reflected towards the receiving transducer in the area close to the slot than in the remote area.

This reduction of sensitivity offsets partly the reduction caused by abatement in the area remote from the slot.

The receiver gain varies as a function of the scanning depth, so as to detect signals with an amplitude capable of modulating the electron beam of the visualization tube. The gain correction will be therefore smaller with two arrays placed side by side.

Referring now to FIGS. 9 and 10, the whole unit of a device according to the first series of embodiments of the invention comprising either a single array common for the transmission and the reception (FIG. 9), or two distinct arrays for the transmission and the reception (FIG. 10) will now be briefly described.

In FIG. 9 has been shown a device with a single array formed substantially of three units, viz.:

a probe 21 comprising a single array 11 with a series of transducers arranged side by side according to a curved band, the center of curvature of which is at 19, with a screen, not shown, comprising a lens (not shown) around 19; one sees in FIG. 9 the electric conductors 22, namely a conductor for each transducer, an electronic unit 23 connected by a cable 24 to probe 21 (in fact to the conductors 22 of said probe) comprising the transmitter, the sequential switches and the receiver, a visualization oscilloscope 25 on the screen 26 of which one sees the image 27 of the object under observation.

The section reconstituted on the screen is homothetic to the analyzed section.

In the instant case, it is the heart 28 of a patient 29 which is observed, the heart being observed through the rib cage 30 the ribs 31 of which are seen crossed with difficulty by the ultrasounds; the contact between aparatus 21, 23, 25, in particular probe 21, and the patient is provided through the skin 32 in a very small area of a few cm$^2$ surrounding the center of curvature 19, namely at the level of the lens arranged around said center.

In FIG. 10 has been shown a more complex device according to the first series of embodiments of the invention, comprising two arrays 11A and 11B, the first being intended for the transmission and the second for the reception of the ultrasonic beams. In order to simplify the figure, a single slot 18 only has been shown at the level of which is arranged a lens 20 for the ultrasounds. The object to be examined is shown at 33.

In FIG. 10 have been materialized (in solid lines) the there and back paths of travel of the ultrasonic beam 3a corresponding to the formation of one line of the image and those of beam 3b (in dotted lines) corresponding to the formation of the following line.

The device of FIG. 10 comprises:

a released oscillator 34 supplying the transducers 12A of array 11A with a sine wave of a frequency of a few megahertz during from one to a few microseconds, with an amplitude of a few tens of volts, and with increasing and decreasing times very short (shorter than a half period of the sine wave), a receiver 35 amplifying and detecting the signals detected by the receiving transducers 12B of array 11B, a visualization device 25 (cathode ray tube), the image being visible at 27a on screen 25, a double analog switch 36 providing the sequential connections on the one hand between the released oscillator and each of the transmitting transducers 12A and on the other hand between each of the receiving transducers 12B and the pre-amplified of receiver 35.

In the devices of FIGS. 9 and 10, one can operate in a series mode as well as in a parallel mode. In the series mode, the various transducers of array 11 (FIG. 9) or 11A (FIG. 10) are being supplied in succession in such manner as to cause each of the transducers to transmit in succession and cyclically, the reception being also effected in the series mode: each of the transducers of array 11 or 11A receives the ultrasonic signals and transmits, in response, electric signals which are sent in succession and cyclically to unit 35.

If N is the number of elementary transducers and F1 the line frequency (cadence of operation of the released oscillator, that is a few kilohertz), the image cadence is equal to F1/N or 50 to 200 images per second about.

In the parallel mode, there is sent simultaneously electric signals to all of the transducers of array 11 or 11A; the whole section is scanned during the duration of one line. The image cadence is then a function of the operation mode of the switch of the receiving channel, used as a fast chopper; the maximum value obtained being equal to the release cadence of the oscillator.

In FIG. 11 has been illustrated in more detail the device of FIG. 10. In FIG. 11 are seen again the two arrays 11A and 11B with the transducers 12A and 12B respectively, the transmitter 34 for the electric signals, the visualization tube 25, with screen 26 and image 27a supplied by receiver 35. The switching unit 36 of FIG. 8 has been devided into two halves 36A and 36B, one for the transmission (36A) and the other for the reception (36B). Likewise, the unit 37 of FIG. 10 has been divided into two halves 37A for the synchronisation and 37B for the scanning for tube 25. In FIG. 11 have been illustrated the various conductors 22A, connecting each transducer 12A to its power amplifier and adaptation circuit 38, and 22B, connecting each transducer 12B with its low noise preamplifier 35. In this embodiment, it has been preferred to use as many receivers as there are reception channels and to switch the output signals, therefore at a high level, with the standard analog switches, rather than to switch at a very low level the signals provided by the transducers 12B.

In the series mode of utilization, the operation of the device of FIG. 11 is similar to that of the devices with parallel beam probes and sequential scanning.

The generator 34, under the action of the control signals from the synchronisation unit 37A generates sine wave trains of short duration (1 microsecond) which are switched off sequentially towards each of the transducers 12A through switch 36A : if a pulse is applied to a given transducer, the following pulse is applied to the adjacent transducer and to that transducer only, and so forth.

When the transducer 12A has been energized, the signal from the receiver supplied by transducer 12B is the only one to be used for controlling the brilliancy of the visualization tube, through the collective line 40 and the conductor 41.

It will be noted that in the embodiment of FIGS. 9, 10 and 11, the image formed is of the "B" type.

As an alternative, one may realize the transducer arrays with the shape of a portion of a sphere instead of having the shape of a circular band, which allows forming images of the "C" type with the possibility of scanning planes of variable depth and inclination.

One may also effect the simultaneous energizing of several adjacent transducers through signals which are dephased in relation to each other, of predetermined quantities, so as to compensate the phase delays due to the different paths of travel and thereby generate a focused ultrasonic beam. The adjacent beam is obtained by offsetting the energized transducers group in the same manner as previously.

The grouping may be effected in a plane so as to obtain a focused beam in the two transverse directions.

Some practical indications will now be given with reference to a non limitative embodiment, the characteristics being determined for a general application to the medical field.

Since the depth resolution is directly connected to the width of the ultrasonic pulses, the pass-band of the transducers must be very large in order to return during the acoustic electric reconversion, signals with increasing and decreasing times remaining close to those of the triggering pulse (smaller than 10 ns). Such transient responses are obtained either by damping the rear face or preferably by adapting the mechanical impedance (interposition of two plates of convenient nature and thickness between the transducers and the ultrasound propagation milieu). The multilayer mechanical adaptation offers moreover the following advantages: very low global conversion loss of the transducer (close to 3 dB), hence a possible diminution of the transmitting level; great convenience for manufacturing the elementary transducers since they are formed on the rear face of the transducer which is of free access.

The frequency is for instance a frequency of 2 MHz (wave length 0.75 mm), the choice of the frequency resulting from a tradeoff between the lateral definition and the maximum scanning width, tradeoff imposed by the diffraction the effects of which decrease as the frequency increases, or the attenuation which increases with the frequency.

The transducers are realized from a curved machined PZT ceramic plate, of the P1.60 type, chosen for its electric and piezoelectric properties. Their dimensions are of $4 \times 10$ mm with a spacing of 0.2 mm (20 elements under 60°) or $3 \times 10$ mm (20 elements under 45°).

The dimensions of the slot are determined as a function of the wave length, the depth of the field and the desired definition. The lenses are in general of different focal length (from 2.5 cm to 4 cm) in order to increase the depth of field (10 cm). They can be cylindrical or spherical.

Finally, it will be remarked that the essential feature of the first series of embodiments of the invention is the probe which comprises a curved array and the screen formed with at least one slot, said slot or said slots being preferably occupied with a lens or two lenses according to case. Due to this fact, one may transform a device for forming images by means of ultrasounds of the prior type with rectilineal array and no screen into a device according to the invention, by replacing the prior art array with a probe according to the invention and by substituting the rectangular scanning with a sectorial scanning.

According to the invention, this probe is curved, it may be cylindrical or spherical, and in the latter case it provides partial compensation for the diffraction in a transverse direction; it may be formed by a line or band of transducers or by a matrice of transducers.

One may foresee a mechanical system deforming the lens or lenses in order to provide, from the same probe, a fine analysis of the near areas, then the deep areas, from the interface where the screen is arranged, by modifying the radius of curvature, and therefore the focal length, of the lenses. The center of curvature of the probe could be somewhat beyond the probe-skin interface (when internal organs are being examined) in order to provide a more detailed visualization of the areas close to the skin.

In the case of two transducer arrays, such arrays could have different radiuses of curvature.

As regards the electronic control, one may foresee different known types of scanning for transmitting as well as for receiving.

Finally, one may foresee a wall separating the transmitting transducers from the receiving transducers in the case where there are two series of distinct transducers for the transmission and the reception, in order to avoid that the interference ultrasound beams, reflected by the edge of the slot or by the lens strike the receiving transducers. array 59. From each of these transducers 94 starts a conductor 63 leading to an electronic unit 64 comprising (n-2) delay lines. If the successive lines connected to the transducers 62 are referenced $63_1$, $63_2$ ... $63_{(n-1)}$, $63_n$, lines $63_2$ ... $63_{(n-1)}$ alone are connected to delay lines, whereas conductors $63_1$ and $63_n$ are not connected to delay lines so as not to delay the signals reaching the transducers 94 or array 62 which are arranged at the two ends of the latter.

At the output of unit 64 are arranged n conductors 65 grouped in a cable 66 leading to a probe 67 comprising n conductors 68; to each cnductor 65 corresponds a conductor 68. The n conductors 68 lead to n transducers 92 arranged according to a plane array 69 forming the active face of probe 67. It will be noted that to each transducer 94 is connected a transducer 92, either directly (without delay, except that introduced by the connected cnductors) for the two extreme transducers, or with a delay (introduced by the delay lines of unit 64) for the other transducers. The array 69 may either comprise a single series of n transducers 92 operating for the transmission as well as for the reception, or two series of n transducers, the first series being connected to cnductors 68 connected to conductors 65, whereas the second series is connected to conductors 70 which are connected, through a cable 71, to n conductors 72 leading to an electronic unit 73 similar to unit 64, that is comprising (n−2) delay lines. Unit 73 comprises n output conductors 74, each of conductors 74 being connected to a conductor 70 either directly or through a delay line of unit 73.

Said conductors 74 are connected to n transducers 96 of a plane array 75 similar to array 62. The extreme transducers of array 75 are connected without delay to the corresponding extreme transducers of array 69 (for reception), whereas the other transducers of array 75 are connected through a delay line to a transducer corresponding to array 69 for the reception.

The transducers 96 of array 75, when they are energized by the corresponding line 74, transmit ultrasonic waves 76 in an appropriate media 77 similar to milieu 61. These waves are received by N transducers 78 arranged on a curved band 79 similar to band 59. Each transducer 78 is connected via a conductor 79a to a stud 80 of a switch 81 the mobile arm 82 of which rotates, under the control of unit 51, in time relationship with the mobile arm 54. The mobile arm 82 is connected through a conductor 83 to the signal input of a receiver 84 which is also controlled by a control unit 51.

The signal output of receiver 84 is applied, through a conductor 85, to the wehnelt 86 of a cathode tube 87 which receives also the control signals from unit 51 via conductors 88 and 89.

In order to complete the description of FIG. 12, it will be noted that the array 69 is arranged against the object to be examined A, for instance against the rib cage, between two ribs; at 90 has been shown the section which can be analysed and at 91 an elementary ultrasound beam.

The operation of the device of FIG. 12 will now be explained, with reference for the explanations regarding the operation of the electronic lenses, to FIGS. 13 and 15.

On the transmission side, transmitter 52, under the control of unit 51, triggers in succession the N transducers 58 of the curved band 59.

In FIG. 12 has been shown the ultrasonic rays 60 transmitted by transducer 58 which is at the top in FIG. 12. The ultrasonic waves strike simultaneously, under different angles, the n transducers 94 of the plane array 62 which transform them into signals.

The electric signals transmitted by the transducers 94 of array 62, in response to ultrasonic waves 60 transmitted by transducer 58 situated in the upper part of FIG. 12, are carried by lines 63, unit 64, lines 65, cable 66 and lines 68 towards the array 69 of n transducers 92. In said transducers, the electric signals are transformed into ultrasonic waves forming beam 91.

Finally, to the beam of rays 60 transmitted by transducer 58 corresponds the beam 91 transmitted by transducers 92 of array 69, the unit situated between arrays 62 and 69, including the arrays themselves, forming a "transformer".

If first of all it is supposed that said transformer does not comprise, in its unit 64, elements introducing different delays in each of lines 63–65, the situation is that which is shown schematically in FIG. 13, namely that at the source point S (corresponding to the upper transducer 58) the transformer puts in correspondence a secondary source S′ transmitting an opening beam $\theta$ with the opening 90 in FIG. 12. In FIG. 13 are to be seen again the arrays 62 and 69 of transducers 59 and 92 respectively. Between said two arrays has been shown each of the elementary lines of FIG. 12 by conductors 93 in FIG. 13.

A beam of ultrasonic waves of maximum intensity in the axial direction is thereby obtained when S corresponds to a medium transducer 58, but diverging. The lateral definition of the acoustic images obtained from such an ultrasonic beam from the secondary source S′ is of course very bad (one centimetre and more, for instance).

It is for mitigating such a disadvantage that, according to the main characteristic of the second series of embodiments of the invention, there is introduced in line 93 elements 95 introducing delays (they are formed for instance by delay lines of standard type).

Due to the existence of said delay elements 95, the assembly 62, 93, 95, 92 form the equivalent of an ultrasonic lens, provided that the delays are increasing from the ends (upper and lower when looking at FIG. 14) towards the center. In FIG. 14 have been shown, by means of rectangles of increasing length, the delay lines introducing increasing delays; no delay lines have been foreseen at both ends; therefore, the upper transducer 94 is connected to the upper transducer 92 without introduction of delay, and the same applies to the connection between the lower transducers 94 and 92.

In such a case, the acoustic waves transmitted by source S are transformed by the electronic lens illustrated in FIG. 14 into acoustic waves converging at point S″, the whole of delay line 95 forming the equivalent of an acoustic lens focusing the ultrasonic beam transmitted by source S. Likewise, the ultrasonic beams transmitted by sources $S_1$ and $S_2$, for instance by the extreme transducers 58 (whereas source S corresponds to the medium transducers 58), converge at $S'_1$ and $S''_2$ respectively.

In the embodiment of FIG. 15, there has been foreseen instead of the delay lines 94 introducing a fixed delay in each path of travel, a unit 64′ which can introduce variable delays programmable for each line, with the exception of the upper line and the lower line, the unit 64′ being the equivalent to a lens with variable focal length. Under these conditions, one may vary the converging point S″ in FIG. 14 between two extreme positions $S''_a$ and $S''_b$ (FIG. 15).

In all cases, with a unit introducing fixed delays (FIG. 14) or variable delays (FIG. 15), one obtains by means of an array 69 of small dimensions the surface of which can be of the order of 1 $cm^2$, a focused analysis ultrasonic beam of variable direction (the convergence point S″ varying between $S''_1$ and $S''_2$, FIG. 14), but with a reduced depth of field.

Reference is now being made to FIG. 16 in which has been shown only the transmitting portion of the device of FIG. 12, but in more detail.

The transmitter 52 supplies, as hereabove mentioned, in succession the various studs $56_1$ to $56_N$ of switch 55, and thereby through lines 57 successively, transducers $58_1$ to $58_N$.

In FIG. 16 has been shown the transmission, in milieu 61, of the ultrasounds transmitted in succession by transducers $58_1$ to $58_N$ which reach the central transducer 94 of array 62. The paths of travel of the ultrasonic waves reaching the central transducer 94 are different and therefore the time needed for the ultrasounds to travel on said paths are different, the shortest time being that corresponding to the medium path $60_m$, the longest path corresponding to the extreme paths $60_1$ and $60_M$. The path differences are compensated by the delay lines 95 which introduce increasing delays, from the delay $5_{(n-1)}$ introduced by the central line till delay $T_1$ introduced by the extreme lines. Moreover, there is foreseen power amplifiers 98 in each line 93, even in those which do not comprise a delay line, for compensation of the connection and transmission losses and for providing the impedance adaptation between the delay lines and the retransmitting transducers 92 of array 69.

Finally, the time needed for the transmission of the electric signals between each transducer 58 and the corresponding transducer 92 is identical due to the presence of the foreseen delay lines 95, as mentioned hereabove, with decreasing delays from $T_{(n-1)}$ to $T_1$ for compensating the different paths of travel of the ultrasounds in milieu 61 (a similar disposition is foreseen on the receiving side).

In FIG. 16 is shown again the analysis section 90 of the object A to be examined, and one can see the correspondence between angle $\theta_m$ between radiuses $60_1$ and $60_m$ and the explored angle to $\theta_m$ comprised in the analysis section 90.

Reference will finally be made to FIGS. 17 to 22 for completing the explanation of the operation of the device of FIGS. 12 and 16.

In FIGS. 17, 19 and 21 have been illustrated the cases corresponding to the use of a screen formed with one or two openings which can be provided with lenses (according to the first embodiment of the invention), whereas in FIGS. 18, 20 and 22 is shown their equivalent when electronic means are used, FIG. 18 corresponding to FIG. 17, FIG. 20 to FIG. 19 and FIG. 22 to FIG. 21. On said figures, one can see the curved surfaces 11 with transducers 12 of FIGS. 6, 8 and 10, and the curved surfaces 59 and 79 of FIGS. 12 and 16.

FIG. 17 corresponds to the case where a screen 17 is foreseen with an opening which does not comprise a lens in said opening 18. The ultrasonic beam transmitted by the upper transducer 12 in surface 11 is shown hachured in FIG. 17. The electronic equivalent illustrated in FIG. 18 corresponds to the case of FIG. 13, viz. without delay line; the ultrasonic beam corresponding to the upper transducer 58 of array 59 is hachured in said FIG. 18. In said figure are seen again arrays 62 and 69 and lines 93 of FIG. 13. One can see that an analysis beam $91_a$ of very bad quality is obtained, and hence the bad lateral definition of the acoustic images.

Whereas FIG. 17 corresponds substantially to the case of FIGS. 2 and 6, FIG. 19 corresponds to the case of FIG. 7 and the screen 17 and the lens 20 are to be seen again in said figure. By comparing the hachured beam of FIGS. 17 and 19, one establishes the improvement obtained.

Said improvement is established again when comparing FIG. 20 (which is the electronic transposition of FIG. 19) to FIG. 18; said last figure illustrates schematically the device according to the invention comprising a unit 64 with delay lines, said unit corresponding, with arrays 62 and 69, to the ultrasound lens 20 of FIG. 19. A beam 91 is thereby obtained which is similar to that illustrated in FIG. 12 and which provides acoustic images with a good lateral definition.

FIG. 21 corresponds substantially to FIG. 8 with a screen 17 formed with two openings provided with lenses $20_A$ for the transmission and $20_B$ for the reception. In FIG. 22 has been shown the device according to the present invention with two electronic lenses equivalent to lenses $20_A$ and $20_B$, namely the lens 62, 64, 69 for the transmission and the lens 69, 73, 75 for the reception. In FIG. 22 are used the same reference numerals as in FIG. 12.

FIGS. 17 to 22 show clearly the relation between the first series and the second series of embodiments according to the invention, the essential difference being the replacement of ultrasound lenses of the first series by electronic lenses in the second series.

The replacement of focusing ultrasound lenses through electronic lenses allows:

an improvement of the lateral resolution through a tracking focusing;

a total separation, if desired, of the transmission and reception channels, and thereby a considerable diminution of the level interference echos due to the multiple reflections of the acoustic waves;

the division of the apparatus into two parts:

(a) a build-up (transmission) and processing (reception) unit for the electric signals;

(b) a miniature probe 67 formed only of the transmitting-receiving array 69 the contact surface of which with the examined object can be of the order of 1 cm$^2$.

It is recalled that such a configuration has already been used in the "sectorscans" piloted by a computer; in said known devices, the computer determines for each of the analysis directions, the amplitude and phase of the triggering signals for the transmitting transducers on the transmission side; on the reception side, it processes in parallel all the signals from the receiving transducers according to the tracking focusing technique; in said known devices, the number of parallel channels is practically limited to 16 or 20 due to the great complexity of the electronic circuits.

On the contrary, according to the second series of embodiments of the invention, it is possible to have a far greater number of channels, and no computer is needed.

With a device according to the second series of embodiments of the invention, it is possible to provide at the same time:

the build-up of converging ultrasonic beams, of variable propagation direction, the reception with fixed focusing or tracking focusing, in the same direction, by means of a very simple equipment, the (solid or liquid) propagation media 61 and 77 with the two associated transducer series playing the role of an analog computer which can operate with transversal or longitudinal volume (either in a solid or in a liquid) or surface untrasonic waves.

It will be noted that the receiving electronic lens (from the receiving array 69 till array 75, including the electronic unit 73) can operate according to two different modes:

in the fixed focusing mode: a focal length for said electronic lens different to that of the transmitting electronic lens provides a good lateral definition with a great depth of field, the operation being similar to that of the device according to the main patent with two ultrasound lenses;

in the tracking focusing mode: by using in this case programmable delay lines, that is allowing a modification of the various delays according to a predetermined program, the phase distribution varying with the time in such manner that the focusing point moves at the same speed as the ultrasounds; there is obtained a good definition (from 1 to 2 mm) in the total scanning area but at the cost of a larger opening and therefore of a larger contact surface.

Finally, it will be noted that transducers 58 and 78 of the curved surfaces 59 and 79 respectively, which are N in number (N can be comprised between 20 and 40 for instance) have a width superior to $\lambda$ ($\lambda$ representing the ultrasonic wave length which is of the order of 0.75 mm), whereas the transducers 94, 92 and 96 of array 62, 69 and 75 respectively, which are n in number (n can be between 20 and 40), have a width inferior to $\lambda$, for instance of $\lambda/2$.

As is obvious and as results from the above explanations, the invention is by no way limited to the applications and embodiments which have been more specifically envisaged; on the contrary, it encompasses all the alternatives.

We claim:

1. A device for forming images through ultrasonic echography comprising in known manner one or two series of individual transducers transmitting, in response to triggering electric signals, ultrasonic signals towards an object to be examined and/or transforming receiving ultrasonic signals into electric signals, means for applying triggering electric signals to the single series of transducers or to the series providing transmission of ultrasonic signals, and means for forming an image from the electric signals supplied by the single series of transducers or the series of transducers receiving the ultrasonic signals, wherein the single series or each series of transducers is arranged along a curved band in such manner as to direct the ultrasonic rays, for the transmission as well as for the reception, through a reduced area surrounding the center of curvature of the curved band or of each curved bad, and at least one electronic lens formed by a first array of ultrasonic transducers arranged in the vicinity of the center of curvature of the curved band or of each curved band, by differential delay electronic means and by a second ultrasonic transducers array.

2. The device according to claim 1, comprising two curved bands of transducers and two electronic lenses comprising each, a first array of transducers arranged in the vicinity of the center of curvature of each curved band, differential delay electronic means and a second array, the second array of the first electronic lens and the second array of the second electronic lends constituting a probe adapted to be placed against the object to be examined.

3. The device according to claim 2, comprising a transmitter supplying in succession and cyclically the transducers of the curved transmitting surface with electric pulses through a first switch, a receiver receiving in succession and cyclically electric pulses from the transducers of the curved receiving surface through a second switch and a control unit controlling the transmitter, the receiver, in in synchronism the two switches.

4. The device according to claim 1, wherein said differential delay electronic means are programmable so as to introduce variable delays in time.

* * * * *

UNITED STATES PATENT AND TRADEMARK OFFICE
CERTIFICATE OF CORRECTION

PATENT NO. : 4,204,435
DATED : May 27, 1980
INVENTOR(S) : Edouard Bridoux et al.

It is certified that error appears in the above—identified patent and that said Letters Patent is hereby corrected as shown below:

Column 16, line 7, "bad" should read -- band --.

Column 16, line 30, "in" (first occurrence) should read -- and --.

Signed and Sealed this

Nineteenth Day of August 1980

[SEAL]

Attest:

SIDNEY A. DIAMOND

Attesting Officer

Commissioner of Patents and Trademarks